(12) United States Patent
Kim (10) Patent No.: US 8,329,862 B1
(45) Date of Patent: Dec. 11, 2012

(54) CELL-KILLING PEPTIDE DERIVED FROM THE C-TERMINUS OF NOXA PROTEIN

(75) Inventor: Tae Hyoung Kim, Gwangju (KR)

(73) Assignee: Chosun University, Gwangju (KR)

( * ) Notice: Subject to any disclaimer, the term of this patent is extended or adjusted under 35 U.S.C. 154(b) by 728 days.

(21) Appl. No.: 10/599,325

(22) PCT Filed: Mar. 22, 2005

(86) PCT No.: PCT/KR2005/000827
§ 371 (c)(1),
(2), (4) Date: Sep. 26, 2006

(87) PCT Pub. No.: WO2006/001582
PCT Pub. Date: Jan. 5, 2006

(30) Foreign Application Priority Data

Mar. 27, 2004 (KR) .................. 10-2004-0020999

(51) Int. Cl.
C07K 19/00 (2006.01)
C07K 7/06 (2006.01)
A61K 38/06 (2006.01)
A61P 35/00 (2006.01)
C12N 15/09 (2006.01)
C07H 21/04 (2006.01)

(52) U.S. Cl. ..... 530/328; 435/69.7; 514/18.9; 514/19.3; 514/21.6; 536/23.4

(58) Field of Classification Search .................. None
See application file for complete search history.

(56) References Cited

U.S. PATENT DOCUMENTS

2003/0224986 A1* 12/2003 Korsmeyer et al. ............. 514/12

FOREIGN PATENT DOCUMENTS

WO 03/097671 11/2003
WO 2004/022580 3/2004

OTHER PUBLICATIONS

NCBI Entrez Protein Database Record for Locus Q7QR31 (Dec. 15, 2003). 2 pages as printed.*
Pinilla et al, 1994 (Biochem J. 301: 647-853).*
Futaki et al, 2001 (Journal of Biochemistry. 276(8): 5836-5840).*
Thorburn et al, Jan. 2004 (Apoptosis. 9(1): 19-24).*
Definition of "fusion protein" in the Dictionary of Cancer Terms from the National Cancer Institute, http://www.cancer.gov/dictionary/?CdrID=44591, printed Oct. 4, 2010, 1 page as printed.*
Seo et al, 2009. Cancer Res. 69(21): 8356-8365.*
Arap et al (1998. Science. 279: 377-380).*
Krenning et al. Ann NY Acad Sci. 1014: 234-245.*
Maina et al, 2006. Cancer Imaging. 6: 153-157.*
Futaki et al, 2003. Journal of Molecular Recognition. 16: 260-264.*
Kueltzo et al, 2003. J Pharm Sci. 92: 1754-1772.*
Deshayes et al, 2004. Biochemistry. 43: 1449-1457.*
Mai, J.C. et al., "A Proapoptotic Peptide for the Treatment of Solid Tumors," Cancer Research, Nov. 1, 2001 (vol. 61, pp. 7709-7712).
Seo, Y.W. et al., "The Molecular Mechanism of Noxa-induced Mitochondrial Dysfunction in p53-Mediated Cell Death," The Journal of Biological Chemistry, Nov. 28, 2003 (vol. 278, No. 48; pp. 48292-48299) (indicated as previously published Sep. 18, 2003).
Cao, G. et al., "In Vivo Delivery of a Bcl-xL Fusion Protein Containing the TAT Protein Transduction Domain Protects against Ischemic Brain Injury and Neuronal Apoptosis," The Journal of Neuroscience, Jul. 1, 2002 (vol. 22, No. 13; pp. 5423-5431).

* cited by examiner

Primary Examiner — Zachary Howard
(74) Attorney, Agent, or Firm — Nath, Goldberg & Meyer; Joshua B. Goldberg (57) ABSTRACT

The present invention relates a novel cell-killing peptide, particularly to a cell-killing peptide that exploits a specific region at the C-terminus of Noxa protein, a "BH3-only" member of Bcl-2 family causing apoptosis and fusion proteins containing the same.

According to the present invention, the cell-killing peptide (CKP) effectively kills a cancer cell such as HeLa or HCT116 when it is conjugated with PTD or CTD domain. Therefore, the cell-killing peptide of the present invention is still stronger to kill cells, compared with conventional substances such as TRAIL, and will be applied widely for various cell therapies, especially in cancer treatment.

5 Claims, 6 Drawing Sheets

SEQUENCE LISTING

<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<223> OTHER INFORMATION: cell-killing peptide

<400> SEQUENCE: 1

```
Lys Leu Leu Asn Leu Ile Ser Lys Leu Phe
  1               5                  10
```

<210> SEQ ID NO 2
<211> LENGTH: 30
<212> TYPE: DNA
<213> ORGANISM: Artificial Sequence
<220> FEATURE:
<223> OTHER INFORMATION: cell-killing peptide coding sequence

<400> SEQUENCE: 2

```
aaacttctga atctgatatc caaactcttc                                         30
```

<210> SEQ ID NO 3
<211> LENGTH: 9
<212> TYPE: PRT
<213> ORGANISM: Artificial Sequence
<220> FEATURE:
<223> OTHER INFORMATION: protein transduction domain

<400> SEQUENCE: 3

```
Arg Arg Arg Arg Arg Arg Arg Arg Gly
  1               5
```

<210> SEQ ID NO 4
<211> LENGTH: 21
<212> TYPE: PRT
<213> ORGANISM: Artificial Sequence
<220> FEATURE:
<223> OTHER INFORMATION: fusion protein

<400> SEQUENCE: 4

```
Arg Arg Arg Arg Arg Arg Arg Arg Gly Arg Gln Lys Leu Leu Asn Leu
  1               5                  10                  15

Ile Ser Lys Leu Phe
             20
```

<210> SEQ ID NO 5
<211> LENGTH: 21
<212> TYPE: PRT
<213> ORGANISM: Artificial Sequence
<220> FEATURE:
<223> OTHER INFORMATION: fusion protein

<400> SEQUENCE: 5

```
Arg Arg Arg Arg Arg Arg Arg Arg Gly Arg Gln Lys Ala Leu Asn Leu
  1               5                  10                  15

Ile Ser Lys Leu Phe
             20
```

<210> SEQ ID NO 6
<211> LENGTH: 21
<212> TYPE: PRT
<213> ORGANISM: Artificial Sequence
<220> FEATURE:
<223> OTHER INFORMATION: fusion protein

<400> SEQUENCE: 6

```
Arg Arg Arg Arg Arg Arg Arg Arg Gly Arg Gln Lys Leu Ala Ala Leu
  1               5                  10                  15

Ile Ser Lys Leu Phe
             20
```

<210> SEQ ID NO 7
<211> LENGTH: 21

```
<212> TYPE: PRT
<213> ORGANISM: Artificial Sequence
<220> FEATURE:
<223> OTHER INFORMATION: fusion protein

<400> SEQUENCE: 7

Arg Arg Arg Arg Arg Arg Arg Arg Gly Arg Gln Lys Leu Leu Asn Leu
1               5                   10                  15

Ile Ala Ala Leu Phe
            20

<210> SEQ ID NO 8
<211> LENGTH: 21
<212> TYPE: PRT
<213> ORGANISM: Artificial Sequence
<220> FEATURE:
<223> OTHER INFORMATION: fusion protein

<400> SEQUENCE: 8

Arg Arg Arg Arg Arg Arg Arg Arg Gly Arg Gln Lys Ala Leu Asn Leu
1               5                   10                  15

Ile Ala Ala Leu Phe
            20

<210> SEQ ID NO 9
<211> LENGTH: 21
<212> TYPE: PRT
<213> ORGANISM: Artificial Sequence
<220> FEATURE:
<223> OTHER INFORMATION: Fusion protein

<400> SEQUENCE: 9

Arg Arg Arg Arg Arg Arg Arg Arg Gly Arg Gln Lys Ala Ala Asn Leu
1               5                   10                  15

Ile Ser Lys Leu Phe
            20

<210> SEQ ID NO 10
<211> LENGTH: 21
<212> TYPE: PRT
<213> ORGANISM: Artificial Sequence
<220> FEATURE:
<223> OTHER INFORMATION: Fusion protein

<400> SEQUENCE: 10

Arg Arg Arg Arg Arg Arg Arg Arg Gly Arg Gln Lys Leu Leu Asn Ala
1               5                   10                  15

Ile Ser Lys Leu Phe
            20

<210> SEQ ID NO 11
<211> LENGTH: 21
<212> TYPE: PRT
<213> ORGANISM: Artificial Sequence
<220> FEATURE:
<223> OTHER INFORMATION: Fusion protein

<400> SEQUENCE: 11

Arg Arg Arg Arg Arg Arg Arg Arg Gly Arg Gln Lys Leu Leu Asn Leu
1               5                   10                  15

Ile Ser Lys Ala Phe
            20

<210> SEQ ID NO 12
<211> LENGTH: 36
```

```
<212> TYPE: PRT
<213> ORGANISM: Artificial Sequence
<220> FEATURE:
<223> OTHER INFORMATION: Fusion protein

<400> SEQUENCE: 12

Arg Arg Arg Arg Arg Arg Arg Arg Gly Asn Ile Ala Arg His Leu Ala
 1               5                  10                  15

Gln Val Gly Asp Ser Met Asp Arg Arg Gln Lys Leu Leu Asn Leu Ile
            20                  25                  30

Ser Lys Leu Phe
        35

<210> SEQ ID NO 13
<211> LENGTH: 36
<212> TYPE: PRT
<213> ORGANISM: Artificial Sequence
<220> FEATURE:
<223> OTHER INFORMATION: Fusion protein

<400> SEQUENCE: 13

Arg Arg Arg Arg Arg Arg Arg Arg Gly Asn Ile Ala Arg His Leu Ala
 1               5                  10                  15

Gln Val Ala Asp Ser Met Asp Arg Arg Gln Lys Leu Leu Asn Leu Ile
            20                  25                  30

Ser Lys Leu Phe
        35

<210> SEQ ID NO 14
<211> LENGTH: 4
<212> TYPE: PRT
<213> ORGANISM: Artificial Sequence
<220> FEATURE:
<223> OTHER INFORMATION: peptide ligand for cancer receptor

<400> SEQUENCE: 14

Glu Pro Pro Thr
 1

<210> SEQ ID NO 15
<211> LENGTH: 4
<212> TYPE: PRT
<213> ORGANISM: Artificial Sequence
<220> FEATURE:
<223> OTHER INFORMATION: side chain of cell-killing peptide

<400> SEQUENCE: 15

Gly Phe Leu Gly
 1
```

CELL-KILLING PEPTIDE DERIVED FROM THE C-TERMINUS OF NOXA PROTEIN

TECHNICAL FIELD

The present invention relates a novel cell-killing peptide (hereinafter, referred to as "CKP"), particularly to a cell-killing peptide which is derived from a specific region at the C-terminus of Noxa protein, a "BH3-only" member of Bcl-2 family causing apoptosis, and fusion proteins containing the same.

The official copy of the sequence listing is submitted as an ASCII formatted sequence listing in a computer readable format with a file name "Sequence_Listing_042211.txt", created on Apr. 22, 2011, and having a size of 5 kilobytes and is filed on Apr. 22, 2011. The sequence listing contained in this ASCII formatted document is part of the specification and is herein incorporated by reference in its entirety.

BACKGROUND ART

Apoptosis is referred to programmed cell death in a multicellular organism and plays a physiological role to grow a normal cell, to maintain cell homeostasis, to prevent cancer and other diseases and to protect a living body from viral or bacterial infection.

Some Bcl-2 family proteins including Bax, Bad, Bak, Bid and Noxa are reported to stimulate apoptosis and have a Bcl-2 homology domain such as BH1, BH2, BH3 and BH4. Especially, Noxa protein is a "BH3-only" member of Bcl-2 family and first discovered in a mouse cell after exposed by X-ray. Also, it is already reported to mediate p53-activated apoptosis (Oda E. et al., Science 288 (5468): 1053~8, 2000). BH3 is a well-known domain in Bcl-2 family and plays a critical role to induce apoptosis. It is also reported that BH3 domain derived from Bid protein may cause apoptosis by peptide itself (Letai et al., Cancer cell 2: 183~192, 2002).

In human, it is elucidated that Noxa regulates the function of mitochondria to stimulate apoptosis. The present inventor has found a mitochondria targeting domain (hereinafter, referred to as "MTD") at the C-terminus of Noxa protein, separate from BH3 domain acting on apoptosis (Seo et al., JBC 278: 48292~48299, 2003). In detail, Noxa protein triggers cytochrome C discharge from mitochondria, activates caspase and kills cells. MTD domain is essential to transport Noxa toward mitochondria and may lose the cell killing activity if deleted, although BH3 domain exists. Therefore, MTD domain is considered to play an important role to kill cells. Nevertheless, it is also reported that only MTD domain without BH3 domain did not bring about apoptosis.

The present inventor has identified that MTD domain, a C-terminal region of Noxa protein that is known to assist BH3 domain for targeting mitochondria, strongly killed cancer cell lines (including HeLa, PC3, A549, HEK 293, and HCT 116) when combined with R8, a protein transduction domain (hereinafter, referred to as "PTD"), tried to develop a novel cell-killing peptide (CKP) and completed the invention successfully.

DISCLOSURE OF THE INVENTION

Therefore, the main object of the present invention is to provide a new cell-killing peptide derived from the C-terminus of Noxa protein.

Another object of the present invention is to provide a new cell-killing fusion protein that combines the cell-killing peptide with other functional domain.

The other object of the present invention is to provide a pharmaceutical composition that is comprised of the cell-killing fusion protein.

Additional advantages, objects and features of the present invention will be set forth in part in the description which follows and in part will become apparent to those skilled in this art upon examination of the following or may be learned from practice of the invention.

According to an aspect of the present invention, there is provided a cell-killing peptide (CKP), which contains the amino acid sequence of SEQ ID NO: 1 or its homologous sequence having at least 70% of sequence homology.

Preferably, the cell-killing peptide of the present invention which has the homologous sequence is comprised of leucine residues at the 2nd, 3rd, 5th and 9th position of the amino acid sequence. More preferably, the cell-killing peptide may contain the 12th~21st amino acid sequence of SEQ ID NO: 7.

In addition, the present invention provides an oligonucleotide, which contains the nucleotide sequence encoding the cell-killing peptide. The oligonucleotide may be DNA or RNA.

According to another aspect of the present invention, there is provided a cell-killing fusion protein that combines the cell-killing peptide with a protein transduction domain (PTD).

Preferably, in the cell-killing fusion protein of the present invention, the cell-killing peptide may be combined with PTD domain derived from Tat protein of HIV 1, homeodomain of Drosophila antennapedia, transcription regulating protein of HSV VP22, MTS peptide derived from vFGF, penetratin, transportan or Pep-1 peptide. More preferably, the cell-killing peptide can be combined with PTD domain containing the amino acid sequence of SEQ ID NO: 3.

According to another aspect of the present invention, there is provided a cell-killing fusion protein that combines the cell-killing peptide with a cancer targeting domain (hereinafter, referred to as "CTD").

Preferably, in the cell-killing fusion protein of the present invention, the cell-killing peptide may be combined with CTD domain that is selected from a group consisting of ligands specific for cancer receptor, monoclonal antibodies specific for cancer antigens, liposomes, polymers and the like.

According to another aspect of the present invention, there is provided a pharmaceutical composition that is composed of one or more selected from the cell-killing fusion proteins as an effective ingredient.

Preferably, the pharmaceutical composition of the present invention may be used to treat cancer.

Hereinafter, the present invention will be described more clearly as follows.

The present invention provides a cell-killing peptide (CKP), which contains the amino acid sequence of SEQ ID NO: 1 or its homologous sequence having over 70% of sequence homology.

In the present invention, the peptide that is known as a mitochondria targeting domain (MTD) in Noxa protein inducing apoptosis, is firstly found to kill cancer cell efficiently and named as cell-killing peptide (CKP). The cell-killing peptide derived from the above-mentioned Noxa protein has the amino acid sequence (KLLNLISKLF) of SEQ ID NO: 1.

The cell-killing peptide of the present invention can be synthesized chemically by the conventional process for peptide synthesis, including solid peptide synthetic method by Fmoc chemistry. In addition, the cell-killing peptide of the present invention can be manufactured by conventional genetic engineering process, in which an oligonucleotide encoding the cell-killing peptide is synthesized by automatic synthesizer or the nucleotide sequence (NCBI GenBank number: NM_021127) of Noxa gene corresponding to MTD domain (41~50) is amplified selectively by performing polymerase chain reaction (PCR) and then, inserted to a proper cloning vectors, expressed in vivo through transcription and translation and purified.

The cell-killing peptide of the present invention can kill cells, whenever it retains the amino acid sequence homologous to SEQ ID NO: 1 with over 70% of homology. For this purpose, the sequence homology of peptides can be decided by using the conventional computer programs, when the natural sequence and variant sequences are compared. Preferably, GAP computer program version 6.0 as Devereux et al. demonstrated (*Nucl. Acids Res.* 12: 387, 1984) can be used and purchased from University of Wisconsin Genetics Computer Group (UWGCG). GAP program is managed by Needleman and Wunsch's array method (*J. Mol. Biol.* 48: 443, 1970) as Smith and Waterman revised (*Adv. Appl. Math* 2: 482, 1981). Therefore, the peptide variants of the present invention are substantially similar to the cell-killing peptide of SEQ ID NO: 1 and becomes partially different from the CKP peptide by deletion, insertion or substitution in 1~3 amino acids. In detail, the amino acid sequence can be varied by substitution between nonpolar amino acid residues (including Ile, Leu, Phe or Trp) or polar amino acid residues (including Gly, Lys, Arg, Glu, Asp, Gln, Asn). The peptide variants are verified to have the cell-killing activity as described in Example 4 and FIG. 6.

Preferably, the cell-killing peptide having over 70% of sequence homology has a feature to contain leucine residues at the 2nd, 3rd, 5th and 9th position of the amino acid sequence. In the cell-killing peptide of SEQ ID NO: 1, the leucine residue is repeated at the 2nd, 3rd, 5th and 9th amino acids of the sequence. The repeated leucine resides are verified to play an important role in the cell-killing activity as described in Example 4 and FIG. 6.

In order to attain the effect of the present invention, the cell-killing peptide should be introduced into cells before it causes cell death. Several methods may be used to inject the peptide into cells. For example, the mechanical method such as electroporation and microinjection (Wong, T. K. & Neumann E., *Biochem. Biophys. Res. Commun.* 107: 584~587, 1982) the fusion method such as vehicle conjugation and liposome fusion [Celis J. E., ed. in Cell Biology: a laboratory handbook, 2nd. ed., Vol. 4., 1998 (Acad Press, San Diego, Calif.)]; the chemical method such as utilization of ATP or EDTA (Rozengurt E., et al., *Biochem. Biophys. Res. Commun.* 67: 1581~1588, 1975) the method for adding pore-forming toxin such as α-toxin of *Staphylococcus aureus* (Grant N. J., Aunis D. and Bader M. F., Neuroscience 23: 1143~1155, 1987); and the like can be exploited.

In order to attain another object, the present invention provides an oligonucleotide that is comprised of DNA or RNA and contains the nucleotide sequence encoding the cell-killing peptide. In a preferred embodiment of the present invention, the oligonucleotide can be the nucleotide sequence of SEQ ID NO: 2 derived from the 3' terminal region of human Noxa gene.

In order to attain another object, the present invention provides a cell-killing fusion protein that combines the cell-killing peptide with a protein transduction domain (PTD). In the present invention, "fusion protein" is understood to include not only fusion protein but also fusion peptide in terms of amino acids length.

In order to introduce the cell-killing peptide into target cells effectively, especially by permeable peptide transduction, the fusion protein of the present invention is prepared by combining the cell-killing peptide with protein transduction domain (PTD). PTD domain helps the fusion protein penetrate across cell membrane, since a lot of basic amino acids including lysine and arginine exist in the sequence.

Preferably, PTD domain can be derived from Tat protein of HIV 1, homeodomain of *Drosophila antennapedia*, transcription regulating protein of HSV VP22, MTS peptide derived from vFGF, penetratin, transportan, Pep-1 peptide or the like. More preferably, PTD domain can contain the amino acid sequence of SEQ ID NO: 3 comprising contiguous 8 arginines synthesized artificially.

The cell-killing fusion peptide of the present invention can be manufactured by the conventional process for peptide synthesis, due to the small number of amino acid residues in the sequence. Preferably, the cell-killing fusion peptide of the present invention can be synthesized chemically by the solid peptide synthetic method using Fmoc chemistry. Also, the cell-killing fusion peptide of the present invention can be manufactured by the process: (1) adopting a common expression vector such as pTAT vector that can produce an exogenous protein combining with PTD (Embury J. et al., *Diabetes* 2001); (2) constructing a recombinant vector that the nucleotide sequence encoding CKP peptide is inserted; (3) expressing PTD-CKP fusion protein in vivo and (4) purifying.

In the present invention, the cell-killing fusion protein is produced directly by the process that combines PTD domain R8G to the N-terminus of CKP peptide and makes CKP peptide transport into cells. Preferably, the fusion protein is comprised of the amino acid sequence of SEQ ID NO: 4. At this moment, R8 designates 8 arginines and (RQ) denotes a linker sequence.

In order to attain another object, the present invention provides a cell-killing fusion protein that combines the cell-killing peptide with a cancer targeting domain (CTD).

In the present invention, the cell-killing fusion protein is produced directly by the process that combines CTD domain to CKP peptide in order to introduce CKP peptide selectively into target cancer cells. Preferably, the cancer targeting domain can be not only ligands or mono/polyclonal antibodies that can recognize receptors, antigens or the like expressed onto the surface of cancer cell, but also polymers permeating a blood vessel in cancer tissue, liposome penetrating cell membrane or the like. At this moment, "antibody" designates a antibody-like molecule having a antigen binding site and can be selected among Fab' Fab, F(ab').sub.2, single domain antibodies (DABs), Fv, scFv (single chain Fv), linear antibodies, diabodies or the like. In the present invention, "fusion" means conjugation, encapsulation and the like and the partner of CKP peptide in the "fusion protein" can be chemical substances instead of amino acids. Preferably, CTD domain can be selected among bombesin and short tetrapeptide (EPPT) (SEQ ID NO:14) targeting mammary cancer antigen, single chain antibody fragment (scFv) specific for prostate gland antigen (PSA), anti-CEA monoclonal antibody specific for epithelial cancer antigen CEA, anti-EGF-R monoclonal antibody targeting EGF receptor specific for cancer cell, anti-HER2 SL targeting HER2 specific for cancer cell, other monoclonal antibodies (including mAb CD20, mAb HER2, mAb CD33, mAb 105), vascular-targeting agents (including ZD6126, AVE8062, Oxi4503), liposomes, PEG (polyethylene glycol), HPMA (N-(2-Hydroxypropyl) methacrylamide) copolymer and the like.

The cell-killing fusion peptide of the present invention can be manufactured by the conventional process for peptide synthesis, whenever its sequence has the small number of amino acid residues. Preferably, the cell-killing fusion peptide of the present invention can be synthesized chemically by the solid peptide synthetic method using Fmoc chemistry. Besides, when the sequence has the large number of amino acid residues, the cell-killing fusion peptide of the present invention can be manufactured by the process: (1) amplifying the gene encoding monoclonal antibody by polymerase chain reaction (PCR); (2) manufacturing the oligonucleotide encoding CKP peptide by automatic synthesizer or amplifying the oligonucleotide by PCR; (3) conjugating both the gene encoding monoclonal antibody and the oligonucleotide in frame; (4) constructing a recombinant vector that the resulting gene is inserted into a proper vector; (5) expressing CTD-CKP fusion protein in vivo through transcription and translation; and then (4) purifying (Zhao J. et al., *J. Biol Chem.* Mar. 5, 2004). Furthermore, the cell-killing fusion peptide of the present invention can be manufactured by the process encapsulating CKP peptide with PEG-coated liposome (Sharpe M. et al., *Drugs.* 62(14): 2089~126, 2002). In addition, the cell-killing fusion peptide of the present invention can be made by the process binding CKP peptide and monoclonal antibody conjugate onto a side chain of oligopeptide in HPMA copolymer (Kovar M. et al., *J. Control Release.* 92(3): 315~30, Oct. 30, 2003).

One or more linker sequence can be added to between CKP peptide and PTD or CTD domain in the cell-killing fusion peptide of the present invention. Preferably, the linker sequence can be an amino acid sequence or intracellular degradable chemical linkage that cannot block the cell-killing activity of CKP peptide.

In order to attain another object, the present invention provides a pharmaceutical composition that is composed of one or more selected from the cell-killing fusion proteins as an effective ingredient.

Preferably, the pharmaceutical composition of the present invention has a feature to be useful for cancer therapy.

Depending on the desired uses of substance according to the present invention, one or more commonly used components such as vehicle can be added through the conventional procedure.

The substance of the present invention can be provided as a main pharmacologically active component in an oral dosage form including, but not limited to, tablets, capsules, caplets, gelcaps, liquid solutions, suspensions or elixirs, powders, lozenges, micronized particles and osmotic delivery systems; or in a parenteral dosage form including unit administration or several times administration.

The dosage of the substance of the invention will vary, depending on factors such as severity of disease or symptom, age, sex, physical condition, administration period, administration method, discharge ratio, body weight, diet and so on. Preferably, the pharmaceutical composition of the present invention can be administered to an adult patient in the range of 10~100 mg per day.

Consequently, the cell-killing peptides of the present invention are identified to kill cancer cells (including HeLa cell) effectively, when CKP peptide is combined with PTD or CTD domain. However, it is not clear about the pathway that the peptides of the present invention may act on cell death. In practice, this cell-killing effect is often stronger than typical apoptosis.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Practical and presently preferred embodiments of the present invention are illustrated as shown in the following Examples. However, it will be appreciated that those skilled in the art, on consideration of this disclosure, may make modifications and improvements within the spirit and scope of the present invention.

EXAMPLE 1

Synthesis of Peptide

In order to synthesize CKP peptide, manual Fmoc synthetic method using 0.25 mmol Unit was basically adopted. In detail, resin was washed by using 4×DMF, blended with 10 ml of 20% piperidine/DMF solution for 1 minute and separated to remove supernatant. After that, the resulting resin was mixed again with 10 ml of 20% piperidine/DMF solution, shaken for 30 minutes and then washed by using 4×DMF. Ninhydrin test was performed to identify whether piperidine remains or not. Resin appeared blue color when without piperidine. In order to proceed a coupling step, a solution comprising 1 mmol of Fmoc-amino acid, 2.1 ml of 0.45 M HBTU/HOBT (1 mmol) and 348 μl of DIEA (2 mmol) was prepared. Resin was blended with the solution, stirred for 30 minutes, poured out to discard the solution and then washed by using 4× DMF. In order to perform a coupling of amino acids, the coupling step mentioned above was repeated and as a result, CKP peptide of SEQ ID NO: 4 (RRRRRRRRGRQKLLNLISKLF) combined with PTD domain was synthesized.

The resulting peptide prepared through the above procedure was characterized by using HPLC (Instrument: Waters 2690 separations module, Flow rate: 1.0 ml/min, Gradient: 0%~20% B 5 minutes 20%~50% B 20 minutes 50%~80% B 5 minutes, A; 0.1% TFA water, B, 0.1% TFA acetonitrile, column: Waters C18, 5 micron, Detection: 220 nm, purity: 95%) and mass spectroscopy (Instrument: HP 1100 series LC/MSD). The synthetic peptide was dissolved in water, adjusted to 1 mM of concentration and stored at −80☐.

EXAMPLE 2

Examination of Cell-Killing Effect of CKP Peptide

Figure 1:
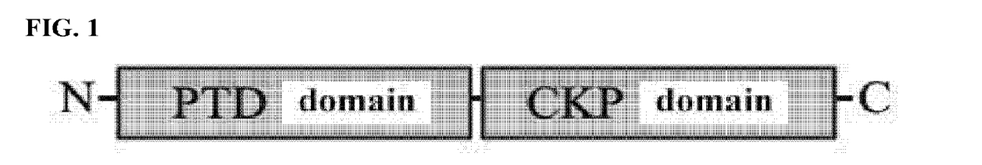
FIG. 1 depicts the schematic diagram of the cell-killing fusion protein that combines CKP peptide with PTD domain.
Figure 2:
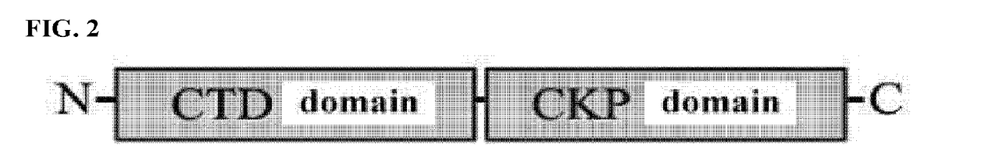
FIG. 2 depicts the schematic diagram of the cell-killing fusion protein that combines CKP peptide with CTD domain.
Figure 3:
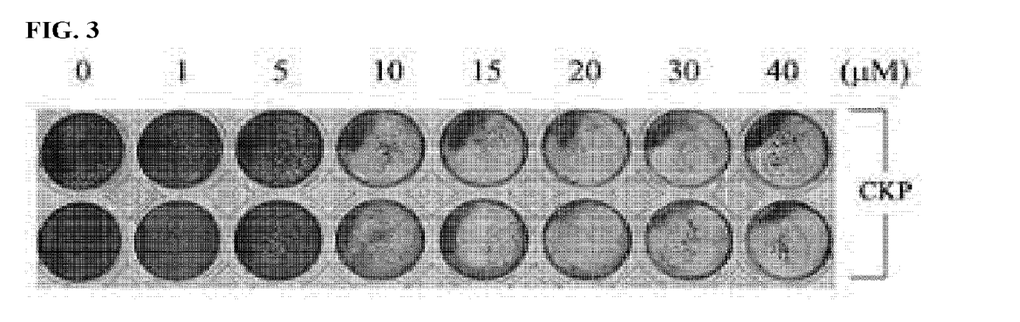
FIG. 3 depicts HeLa cells that are stained by crystal violet after treating CKP peptide of the present invention according to concentrations.

In order to examine the cell-killing effect of CKP peptide synthesized in Example 1, HeLa cell, a cervical cancer cell line was adopted and cultivated. The culture medium was replaced with experimental media containing CKP peptide solution in 0, 1, 5, 10, 15, 20, 30, 40 µM of concentration serially and cultivated for more 24 hours. In order to observe living cells attached on the surface, the resulting cells were stained for 10 minutes by using 100 µl of 0.5% crystal violet and then, washed out by using distilled water and running water to be de-stained, while discarding cells floating on the culture medium. Then, cells were observed by photography after placing culture vessel under a fluorescent lamp box as depicted in FIG. 3. At this moment, living cells attached on the surface appeared blue color since they were stained by crystal violet. As illustrated in FIG. 3, CKP peptide of the present invention is identified to have the cell-killing activity at from 10 µM of concentration remarkably.

EXAMPLE 3

Comparison of Cell-Killing Effects in CKP Peptide and PTD Domain

Figure 4:
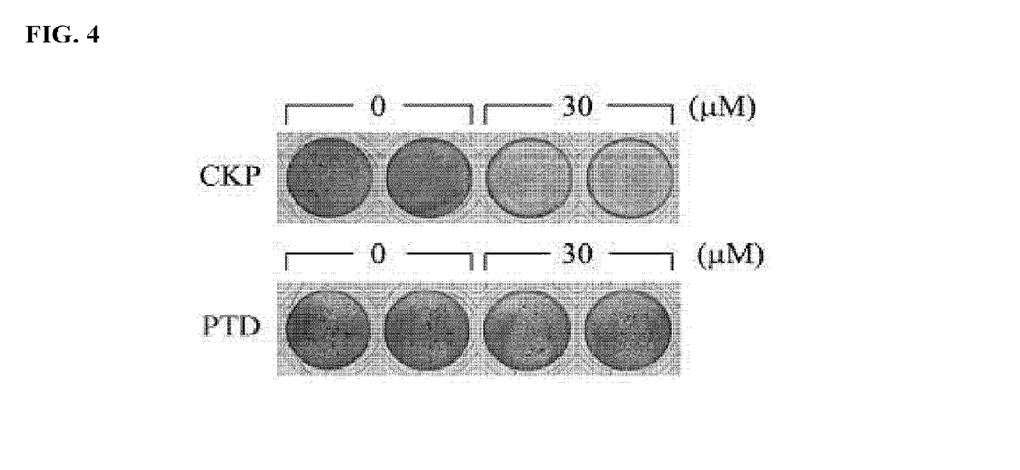
FIG. 4 depicts HeLa cells that are stained by crystal violet after treating CKP peptide of the present invention and PTD domain without CKP domain.
Figure 5:
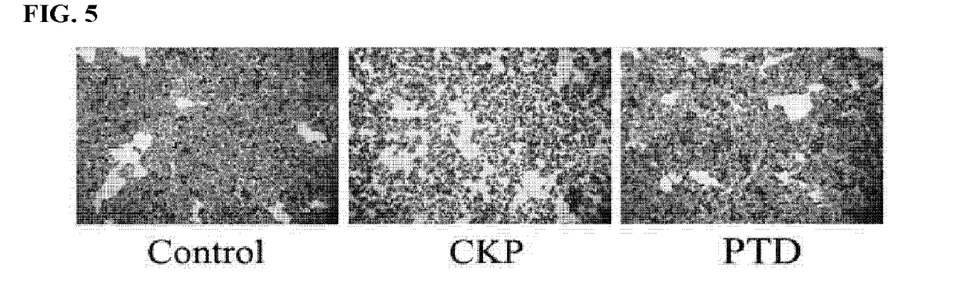
FIG. 5 depicts HeLa cells that are observed by optical microscopy after treating CKP peptide of the present invention and PTD domain without CKP domain.

In order to verify whether CKP peptide affects the cell-killing activity directly or not, only PTD domain without CKP domain was synthesized by the procedure described in Example 1 and used to compare the cell-killing effect with CKP peptide of the present invention. The experiment was performed by the same procedure as demonstrated Example 2. As depicted in FIG. 4, the cell-killing activity was not detected at all when adding PTD domain without CKP domain, but became strong remarkably when treating CKP peptide of the present invention. In order to observe the cell morphology exactly, the culture plates depicted in FIG. 4 were photographed after magnified to 100× by optical microscopy (Nikkon, Model: Optiphot-2, Japan) as shown in FIG. 3. Control denotes HeLa cell without peptide; CKP, CKP peptide-treating cell; and PTD, PTD domain without CKP peptide-treating cell.

EXAMPLE 4

Examination of Cell-Killing Effects of CKP Peptide Variants

In order to examine whether CKP peptide variants retain the cell-killing activity or not, several CKP peptide variants in which 1~3 of amino acid residues are substituted, were synthesized by the procedure described in Example 1. Precisely, CKP peptide CKP 2 (substituted in one residue), CKP 3 (substituted in two residues) CKP 4 (substituted in two residues) and CKP 5 (substituted in three residues) were prepared to contain the amino acid sequence of SEQ ID NO: 5 (RRRRRRRRGRQKALNLISKLF), SEQ ID NO: 6 (RRRRRRRRGRQKLAALISKLF), SEQ ID NO: 7 (RRRRRRRRGRQKLLNLIAALF) and SEQ ID NO: 8 (RRRRRRRRGRQKALNLIAALF) respectively. In order to investigate whether the leucine repeat in the CKP peptide affect the cell-killing activity or not, several CKP peptide variants were synthesized by the procedure described in Example 1. Precisely, CKP peptide CKP 6 (in which the 2nd and 3rd leucines are substituted to alanine), CKP 7 (in which the 5th leucine is substituted to alanine) and CKP 8 (in which the 9th leucine is substituted to alanine) were manufactured to contain the amino acid sequence of SEQ ID NO: 9 (RRRRRRRRGRQKAANLISKLF), SEQ ID NO: 10 (RRRRRRRRGRQKLLNAISKLF) and SEQ ID NO: 11 (RRRRRRRRGRQKLLNLISKAF).

Figure 6:
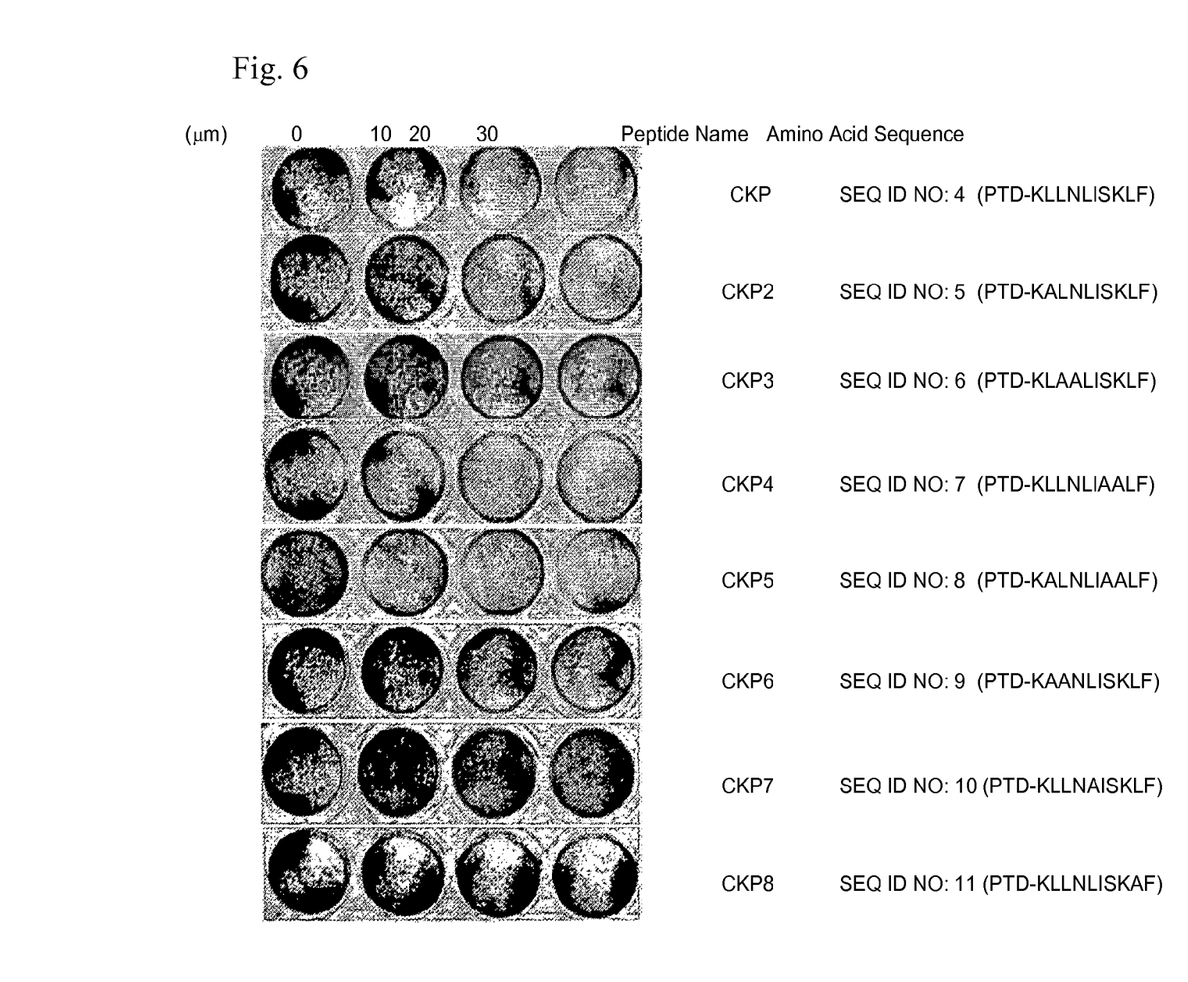
FIG. 6 depicts HeLa cells that are stained by crystal violet after treating CKP peptide identified by SEQ ID NO: 4 and other variant peptides identified by SEQ ID NO: 5 to SEQ ID NO: 11, respectively, according to the present invention.

In order to examine how the variants influence HeLa cell, the cell-killing activity was measured by the procedure described in Example 2 and the experimental data were illustrated in FIG. 6. As a result, CKP 2, CKP 3 and CKP 5 decreased the cell-killing activity slightly, compared with CKP peptide, but CKP 4 had the cell-killing activity outstanding rather than CKP peptide of the present invention. Moreover, CKP 6, CKP 7 and CKP 8 peptide that are substituted in some leucine residues decreased the cell-killing activity remarkably, compared with CKP peptide. Therefore, it is confirmed that the leucine residues of the amino acid sequence play an important role to kill cells in CKP peptide.

EXAMPLE 5

Examination of Cell-Killing Effects of Fusion Proteins Combining CKP Peptide with Other BH 3 Domain In order to examine whether CKP peptide combined with other BH 3 domain, not from Noxa, retains the cell-killing activity or not, a fusion protein that combines CKP peptide with BidBH3 peptide and contains the amino acid sequence of SEQ ID NO: 12 was synthesized and named as BidBH3CKP. In order to observe how the fusion protein affects HeLa cell, the cell-killing activity was measured by the procedure described in Example 2. As a result, it is clarified that BidBH3CKP conjugate has the cell-killing activity 2-fold stronger that BidBH3 peptide as illustrated in FIG. 6.

Figure 11:
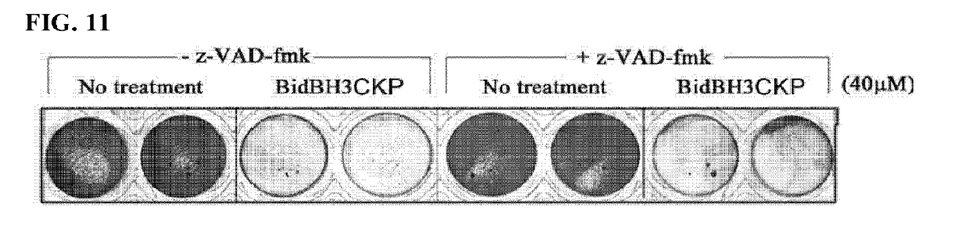
FIG. 11 depicts HeLa cells that are cultivated by using culture media with caspase inhibitor z-VAD-fmk and stained by crystal violet after treating CKP peptide and BidBH3 conjugate (BidBH3CKP) in the present invention.
Figure 12:
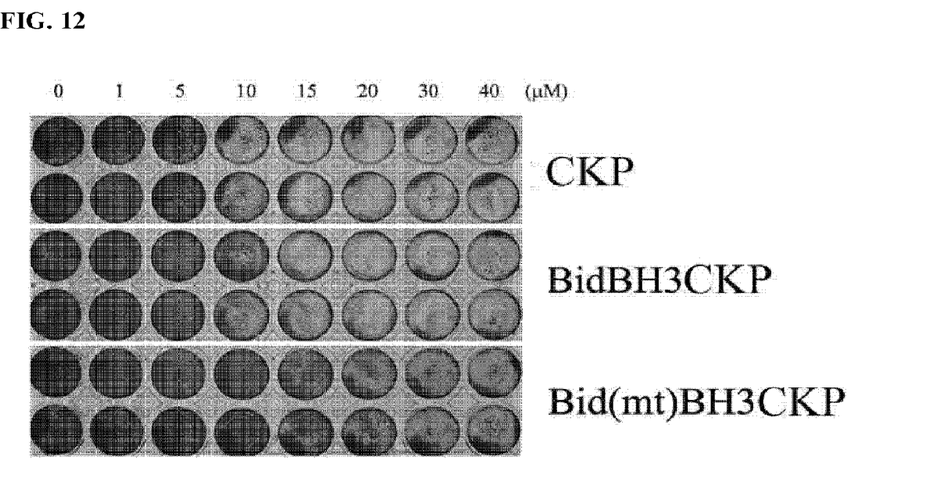
FIG. 12 depicts HeLa cells that are stained by crystal violet after treating CKP peptide and mutant BidBH3 conjugate (Bid(mt)BH3CKP) in the present invention according to concentrations.

Besides, in order to investigate whether the fusion protein depends on caspase for the cell-killing activity or not, a pan-caspase inhibitor, z-VAD-fmk (Calbiochem, USA) was added to culture media alternatively and the cell-killing activities were compared by the procedure described in Example 2. As a result, there is not significant difference of cell-killing activity in between with or without z-VAD-fmk, as illustrated in FIG. 11. Therefore, it is clear that BidBH3CKP conjugate is independent upon caspase for the cell-killing activity.

Furthermore, in order to examine whether BidBH3CKP conjugate causes cell death by BidBH3 domain or by CKP domain, the fusion protein Bid(mt)BH3CKP that combines CKP peptide with mutant BidBH3 deleting the active site of BH3 domain was synthesized to contain the amino acid sequence of SEQ ID NO: 13. In order to examine whether the mutant domain affects HeLa cell or not, the cell-killing activity was measured by the procedure described in Example 2. As a result, mutant Bid(mt)BH3CKP conjugate also had the cell-killing activity as illustrated in FIG. 6. Therefore, it is confirmed that only CKP peptide retains the cell-killing activity.

EXAMPLE 6

Comparison I of Cell-Killing Effects of CKP Peptide, Trail and Cisplatin

Figure 7:
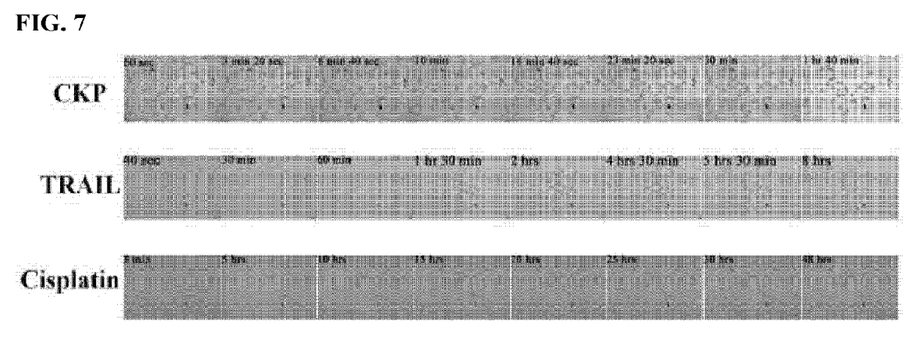
FIG. 7 depicts the comparison of cell-killing effects upon HeLa cells according to time intervals after treating CKP peptide of the present invention, TRAIL or Cisplatin.
Figure 8:
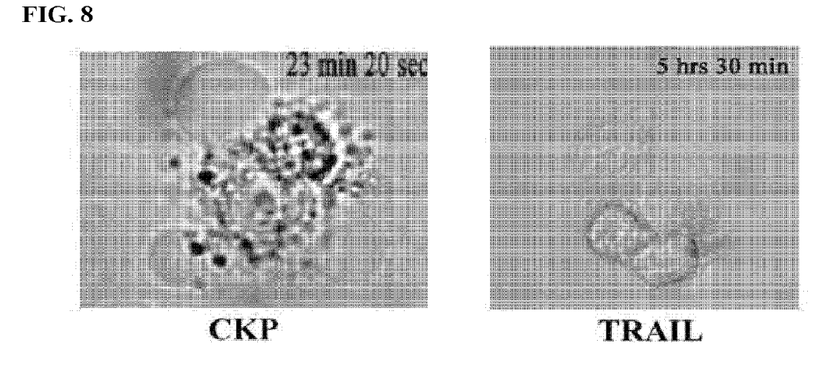
FIG. 8 depicts the comparison of cell-killing effects upon HeLa cells after treating CKP peptide of the present invention and TRAIL and magnifying.

In order to analyze the action mode of CKP peptide of the present invention, several substances that are known to kill cells were adopted to compare the cell-killing effects. Above all, CKP peptide (10 μM), TRAIL (100 ng/ml) and Cisplatin (100 μg/ml) were treated to HeLa cell lines and observed under time-lapse video capture microscopy (Leica, Model: DMIRBE, Germany) in some time-interval (for CKP peptide, 20 seconds; TRAIL, 40 seconds; Cisplatin, 3 minutes) for 1 hour and 40 minutes, 3 hours and 30 minutes, 8 hours and 48 hours respectively. Then, the results were photographed to 40× by using FW4000 software. FIG. 7 depicts HeLa cells serially at each time interval. As a result, it is observed that the cell death caused by TRAIL started at about 1 hour and 30 minutes after treatment and reached the maximum level at about 8 hours. To the contrary, HeLa cell started to die at about 10 minutes after treating CKP peptide and most of HeLa cells have died even at 23 minutes and 20 seconds. As demonstrated in FIG. 8, dead HeLa cells were observed at 23 minutes and 20 seconds after treating CKP peptide through photography to have several cell membranes like balloon. This result of cell-killing mode was different from apoptosis caused by TRAIL or Cisplatin. In the meantime, dead HeLa cells were detected at 5 hours and 30 minutes after treating TRAIL by photography, but not to have cell membrane like balloon through cell death process.

EXAMPLE 7

Comparison II of Cell-Killing Effects in CKP Peptide, Trail and Cisplatin

Figure 9:
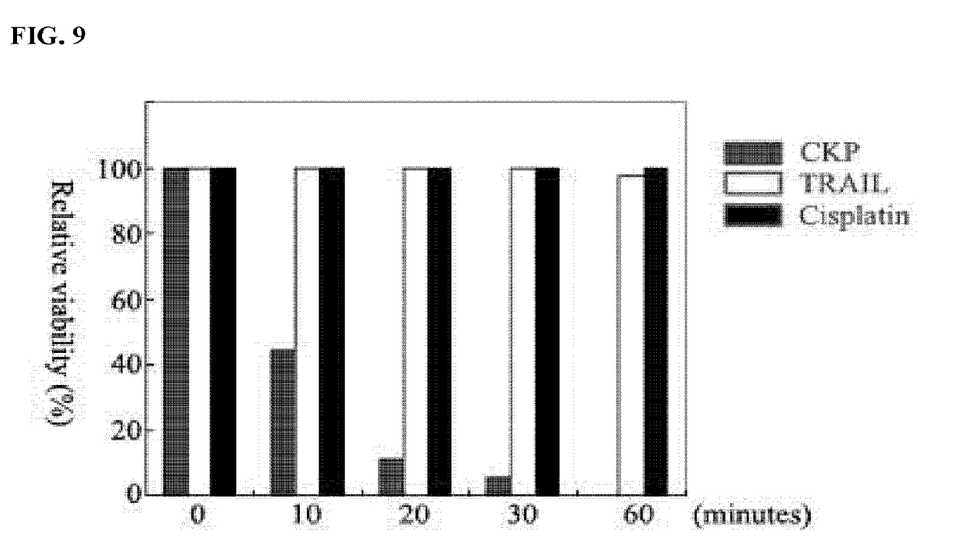
FIG. 9 depicts the relative survival ratio of HeLa cells that is estimated after treating CKP peptide of the present invention, TRAIL and Cisplatin according to concentrations.
Figure 10:
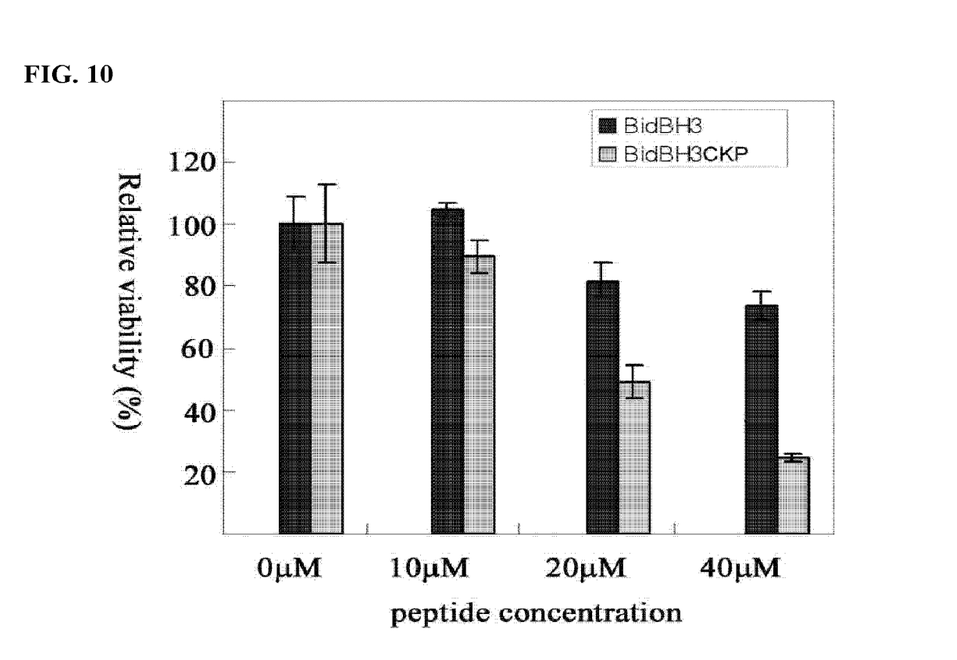
FIG. 10 depicts the relative survival ratio of HeLa cells that is estimated after treating CKP peptide and BidBH3 conjugate (BidBH3CKP) in the present invention according to concentrations.

In order to measure the strength of CKP peptide, several substances that are known to kill cells were adopted to compare the cell-killing effects. HeLa cell, a cervical cancer cell line was cultivated and treated with CKP peptide, TRAIL and Cisplatin to 30 μM, 100 ng/ml and 100 μg/ml respectively for 1 hour. After that, the resulting cells were observed under time-lapse video capture microscopy (Leica, Model: DMI RBE, Germany) in 20 seconds of time-interval for 1 hour by the procedure described in Example 5, photographed to 40×, counted for the numbers of living cells and dead cells and then, estimated the relative survival ratio in a graph. As illustrated in FIG. 9, the cell survival ratio decreased to 0~10% when treating CKP peptide for 1 hour, but maintained to 95~100% when treating TRAIL or Cisplatin. As a consequence, it is clarified that CKP peptide of the present invention had the strongest cell-killing effect about 9-fold more than TRAIL or Cisplatin.

EXAMPLE 8

Examination of Fusion Protein Combining CKP Peptide with Cancer Targeting Domain In order to examine the cell killing effect of fusion protein, HPMA copolymer that is soluble and can permeate the blood vessel in cancer, was conjugated with the CKP peptide by adding it to tetrapeptidic side chain (Gly-Phe-Leu-Gly) (SEQ ID NO:15). HPMA-CKP conjugate synthesized above was purified by HPLC (Instrument: Waters 2690 separations module, Flow rate: 1.0 ml/min, Gradient: 0%~20% B 5 minutes 20%~50% B 20 minutes 50%~80% B 5 minutes, A; 0.1% TFA water, B; 0.1% TFA acetonitrile, column: Waters C18, 5 micron, Detection: 220 nm, purity: 95%) and then, stored at −80° C. until use. MCF-7 cell, a cell line derived from human mammary cancer was injected on nude mice to induce cancer tissue. Then, HPMA-CKP conjugate was administered to the resulting mice while adjusting to 10 μM of blood level. After injecting every other day for 7 days, the size of cancer lesion was measured and injuries on normal tissue were observed in liver, kidney, blood vessel and the like. As a result, the size of cancer lesion decreased in the experimental group injecting HPMA-CKP conjugate remarkably, but continued to increase in control group.

INDUSTRIAL APPLICABILITY

As illustrated and confirmed above, the present invention provides a novel cell-killing peptide (CKP) that exists at the C-terminus of Noxa protein known as "BH3-only" member of Bcl-2 family causing apoptosis, which effectively kills a cancer cell such as HeLa or HCT116 more when it is conjugated with PTD or CTD domain. Therefore, the cell-killing peptide of the present invention is still stronger to kill cells, compared with conventional substances such as TRAIL and will be applied widely for various cell therapies, especially in cancer treatment.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A cell-killing fusion protein comprising: a cell-killing peptide (CKP) fused to a protein transduction domain (PTD), wherein the peptide consists of the amino acid sequence of SEQ ID NO: 1 or an amino acid sequence having at least 70% identity to SEQ ID NO: 1 and the peptide does not contain a BH3 domain of Noxa protein, and wherein the PTD comprises a cell membrane-permeable amino acid sequence.

2. The cell-killing fusion protein according to claim 1 wherein the protein transduction domain (PTD) is derived from one or more selected from the group consisting of Tat protein of HIV-1, penetratin (homeodomain of *Drosophila antennapedia*), VP22 (transcription regulating protein of HSV), membrane translocating sequence (MTS) peptide derived from vFGF, transportan and Pep-1 peptide.

3. The cell-killing fusion protein according to claim 1, wherein the protein transduction domain consists of the amino acid sequence of SEQ ID NO: 3.

4. A cell-killing fusion protein comprising: a cell-killing peptide (CKP) fused to a cancer targeting domain (CTD), wherein the peptide consists of the amino acid sequence of SEQ ID NO: 1 or an amino acid sequence having at least 70% identity to SEQ ID NO: 1 and the peptide does not contain a BH3 domain of Noxa protein, and wherein the CTD comprises a ligand specific for a cancer receptor, wherein the ligand is an amino acid sequence.

5. A pharmaceutical composition comprising the fusion protein according to any one of claims 1 to 4.

* * * * *